United States Patent [19]

Jones, Jr. et al.

[11] Patent Number: 5,248,360
[45] Date of Patent: Sep. 28, 1993

[54] PROCESS FOR PREPARING COMPOSITES BASED ON ORIENTED MESOGENIC THERMOSET RESINS

[75] Inventors: Robert E. Jones, Jr., Clute; Jimmy D. Earls; Robert E. Hefner, Jr., both of Lake Jackson, all of Tex.

[73] Assignee: The Dow Chemical Company, Midland, Mich.

[21] Appl. No.: 830,105

[22] Filed: Feb. 3, 1992

[51] Int. Cl.$^5$ .................... C09K 19/52; C09K 19/38
[52] U.S. Cl. .................... 156/166; 156/180; 156/296; 156/330; 252/299.01; 428/1
[58] Field of Search ............... 156/166, 180, 181, 296, 156/330; 428/1; 252/299.01

[56] References Cited

U.S. PATENT DOCUMENTS

| | | |
|---|---|---|
| 4,479,999 | 10/1984 | Buckley et al. |
| 4,962,163 | 10/1990 | Hefner, Jr. et al. |
| 5,024,785 | 6/1991 | Hefner, Jr. et al. ............ 252/299.01 |
| 5,066,750 | 11/1991 | Hefner, Jr. et al. |
| 5,078,910 | 1/1992 | Litt ............................. 428/1 X |

OTHER PUBLICATIONS

CA 113:173774k.
CA 114:248575c.
Satya Bhama and Samuel I. Stupp, "Grafting of a Liquid Crystal Polymer on Carbon Fibers" *Polymer Engineering and Science*, vol. 30, No. 10, pp. 603–607 (1990).
S. T. Chung, Z. Gurion, and J. B. Stamatoff, "Induced Orientational Behavior of Liquid Crystal Polymer by Carbon Fibers" *Polymer Composites*, vol. 6, No. 3, pp. 181–184 (Jul. 1986).
P. M. Adams and J. J. Mallon, "Liquid Crystal Orientation on Carbon Fibers" *Molecular Crystal Liquid Crystal*, vol. 208, pp. 65–75 (1991).
Satya Bhama and Samuel Stupp, "Liquid Crystal Polymer-Carbon Fiber Composites Molecular Orignta- tion" *Polymer Engineering and Science*, vol. 30, No. 4, pp. 228–233 (Feb. 1990).
N. Avramova and S. Fakirov, "Liquid Crystalline Polymer Laminates" *Journal of Applied Polymer Science*, vol. 42 pp. 979–984 (1991).

*Primary Examiner*—Jeff H. Aftergut

[57] ABSTRACT

Continuous fiber reinforced oriented mesogen-containing resin matrix composites are prepared by (A) saturating a continuous fiber substrate material with a curable composition comprising (1) at least one mesogen-containing resin which contains an average of more than one vicinal epoxide group, thiirane group, cyanate group or vinyl ester group per molecule; and, optionally, (2) a curing amount of at least one curing agent and/or curing catalyst therefor; (B) arranging one or more saturated continuous fiber substrate material(s) formed in step (A) into a desired configuration; (C) subjecting the arranged saturated continuous fiber substrate material(s) from step (B) to a temperature which causes the mesogen-containing resin to convert to a liquid crystalline state; (D) subjecting the heated arranged saturated continuous fiber substrate material(s) from step (C) to a pressure sufficient to cause flow induced shear in the interstices of said continuous fiber substrate; (E) subjecting the continuous fiber substrate material of step (D) to curing conditions either simultaneously with the application of pressure in step (D) and/or subsequent to said application of pressure; and (F) permitting the cured continuous fiber reinforced composite of step (E) to cool to room temperature; thereby forming a cured continuous fiber reinforced composite containing an oriented mesogen-containing resin matrix. These composites have improved properties as compared to composites which are not oriented.

4 Claims, No Drawings

PROCESS FOR PREPARING COMPOSITES BASED ON ORIENTED MESOGENIC THERMOSET RESINS

FIELD OF THE INVENTION

The present invention pertains to a process for orienting a mesogenic thermosettable (curable) resin matrix during the preparation of a continuous fiber reinforced composite and the composite resulting therefrom.

BACKGROUND OF THE INVENTION

Bhama and Stupp in Polymer Engineering and Science, volume 30, number 4, pages 228 to 233 (February, 1990) disclose that carbon fibers dispersed into a thermotropic liquid crystal polyester have an influence on the orientation Of said polyester when a magnetic field is applied to induce orientation. An enhanced rate of magnetic field induced orientation wa3 observed in the molten polyester when carbon fibers were dispersed therein. Bhama and Stupp in Polymer Science and Engineering, volume 30, number 10, pages 603 to 608 (May, 1990) additionally disclose that carbon fibers which have been grafted with thermotropic liquid crystal polyester may be useful to control bonding and molecular orientation in the interfacial regions of the composite.

Buckley, et al. in U.S. Pat. No. 4,479,999 (Oct. 30, 1984) discloses a fabric comprising fusible and infusible fibers wherein said fusible fibers comprise thermotropic liquid crystal polymers. Heating of the liquid crystal fibers induces fusion to the adjacent infusible fibers without substantial loss of the orientation which was imparted to said fibers via melt extrusion.

Chung, Gurion and Stamatoff in Polymer Composites, volume 6, number 3, pages 181 to 184 (July, 1986) disclose that preoriented thermotropic liquid crystal copolyester films are selectively oriented parallel to the carbon fiber axis in compression molded composites prepared using continous carbon fiber. The parallel orientation occurs regardless of the initial direction of preorientation of the liquid crystal copolyester film.

All of the aforementioned employ a thermotropic liquid crystal thermoplastic matrix polymer to form the composite. Because of the extensive use of thermoset resins as composite matrix materials, it would be highly desireable to provide a process wherein a mesogenic thermoset resin matrix is substantially oriented during forming of a composite. Said composites would then provide needed increases in physical, mechanical and/or thermal properties as well as corrosion resistance over conventional thermoset resin based composites.

Current methods for achieving an oriented liquid crystal matrix in a composite system are based on either A.) injection molding or extrusion of blends of thermotropic liquid crystal thermoplastics and chopped fiber reinforcement or B.) consolidation of oriented films of thermotropic liquid crystal thermoplastics and a continuous fiber reinforcement. In the injection molding or extrusion processing methods, the amount of chopped fiber reinforcement is usually limited to 30 weight percent or less in order to maintain processability. This constraint greatly restricts the reinforcement that can be achieved. In the consolidation of oriented films of thermotropic liquid crystal thermoplastics, fiber wetout cannot be achieved without melting of the film. Melting and flow to wetout the fibers can result in partial, if not total loss of the orientation.

The present invention provides a process for orienting a mesogenic epoxy resin matrix during the preparation of a continuous fiber reinforced composite. According to the process of the present invention thermosettable mixtures containing a mesogenic thermoset resin are used to prepare composites wherein said cured resin provides an oriented matrix. Additionally, according to the process of the present invention, high levels of fiber reinforcement (50 weight percent or more) can be used and fiber wetout is achieved prior to and/or during orientation of the matrix.

SUMMARY OF THE INVENTION

A method for forming a continuous fiber reinforced oriented mesogen-containing resin matrix composite which method comprises (A) saturating a continuous fiber substrate material with a curable composition comprising
  (1) at least one mesogen-containing resin which contains an average of more than one vicinal epoxide group, thiirane group, cyanate group or vinyl ester group per molecule; and optionally,
  (2) a curing amount of at least one curing agent and/or curing catalyst therefor;

(B) arranging one or more saturated continuous fiber substrate material(s) formed in step (A) into a desired configuration;

(C) subjecting the arranged saturated continuous fiber substrate material(s) from step (B) to a temperature which causes the mesogen-containing resin to convert to a liquid crystalline state;

(D) subjecting the heated arranged saturated continuous fiber substrate material(s) from step (C) to a pressure sufficient to cause flow induced shear in the interstices of said continuous fiber substrate;

(E) subjecting the continuous fiber substrate material(s) of step (D) to curing conditions either simultaneously with the application of pressure instep (D) and/or subsequent to said application or pressure; and (F) permitting the cured continuous fiber reinforced composite of step (E) to cool to room temperature;

thereby forming a cured continuous fiber reinforced composite containing an oriented mesogen-containing resin matrix.

Another aspect of the present invention concerns the oriented thermoset mesogenic resin and continuous fiber reinforced composites resulting from the aforesaid process as well as products prepared therefrom.

DETAILED DESCRIPTION OF THE INVENTION

Mesogenic Thermosettable resins

Any epoxy, thiirane, cyanate or vinyl ester resin containing an average of more than one epoxide, thiirane, cyanate or vinyl ester group and at least one mesogenic moiety per molecule may be used in the process of the present invention to prepare the composites of the present invention. Suitable thermosettable resins containing at least one mesogenic moiety per molecule include those represented by the Formulas I, II or III;

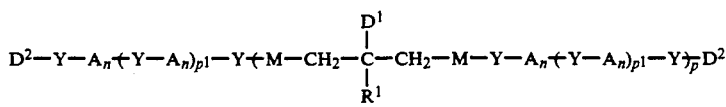 Formula I

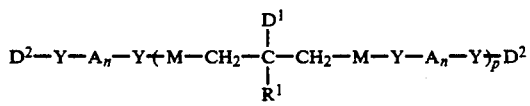 Formula II

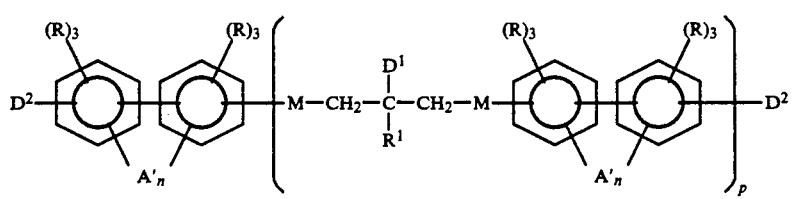 Formula III wherein each Y is independently

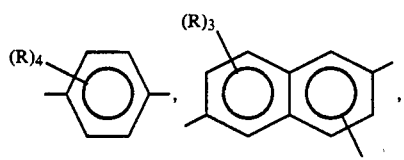

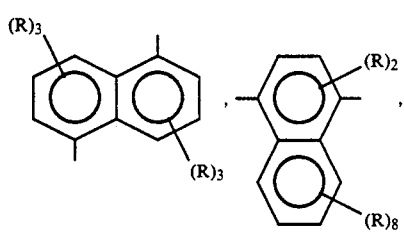

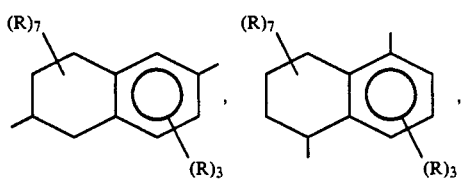

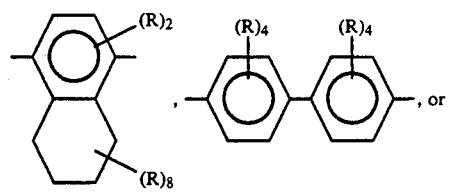

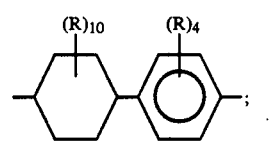

D is —O— or —S—; $D^1$ is —OH or —SH; $D^2$ is

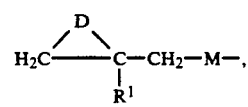

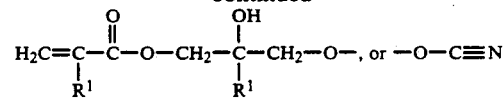

with the proviso that when $D^2$ is —O—C≡N, p has a value of zero and when $D^2$ is

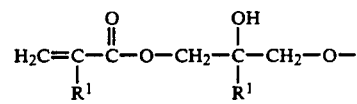

and p has a value greater than zero then $D^1$ is —OH; each M is independently (a) —O—, —S—, —NR$^2$—, or —CO—O— where the single bonded oxygen atom attached to the carbon atom of —CO—O— is attached to the

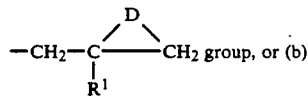 group, or (b)

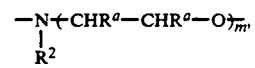

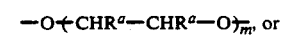

where a single bonded oxygen atom is attached to the

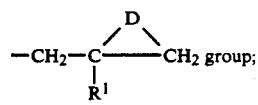 group;

each $R^a$ is independently hydrogen or an alkyl or haloalkyl group containing from 1 to about 2 carbon atoms with the proviso that only one $R^a$ group can be a haloalkyl group; m has a value from 1 to about 100, preferably from 1 to about 20, more preferably from 1 to about 10, most preferably from 1 to about 5; each A is independently a direct single bond, —CR$^1$=CR$^1$—, —C=C—, —N=N—, —CR¹=N—, —O—CO—, —NR¹—,
—CR¹=N—N=CR¹—, —CR¹=CR¹—CO—,
—N=CR¹—, —CO—O—, —CO—NR¹—,
—CO—CR¹=CR¹—, —CO—O—N=CR¹—, —CR¹=N—O—OC—, —CO—NR¹—NR¹=CR¹—,
—CR¹=CR¹—O—OC—, —CO—O—CR¹=CR¹—,
—O—OC—CR¹=CR¹—, —CR¹=CR¹—CO—O—,
—CHR¹—O—CO—CR¹—, —CR¹=CR¹—CO—O—CHR¹—, —CHR¹—CO—O—CR¹=CR¹—, —CR¹=CR¹—O—CO—CHR¹, —CO—S—,
—S—OC—, —CH₂—CH₂—CO—O—, —O—O-C—CH₂—CH₂—, —C≡C—C≡C—,
—CR¹=CR¹=CR¹—,

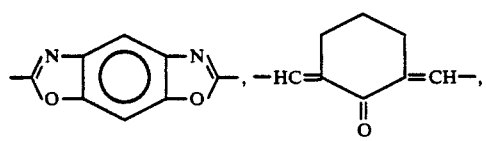, —HC= ... =CH—,

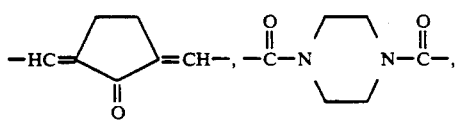

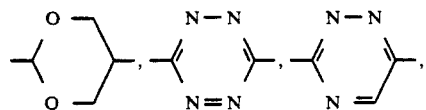

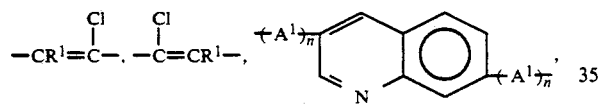

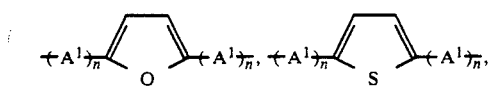

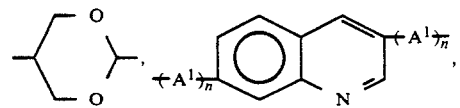

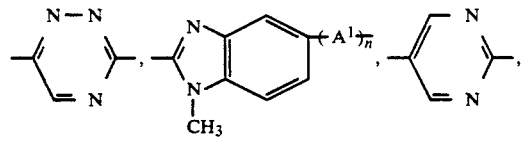

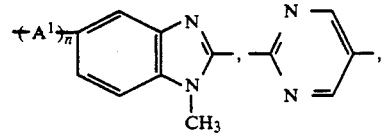

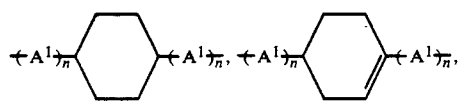

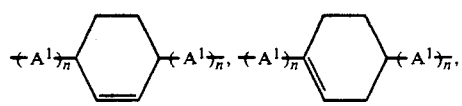

-continued

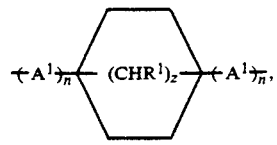

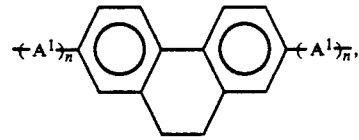

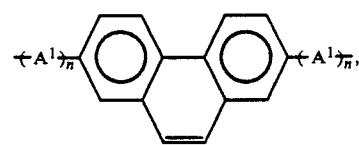

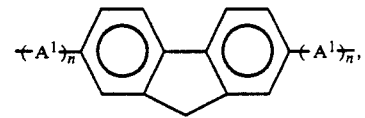

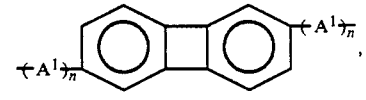

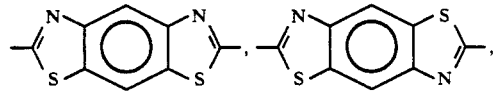

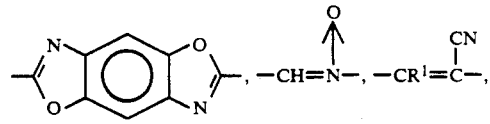

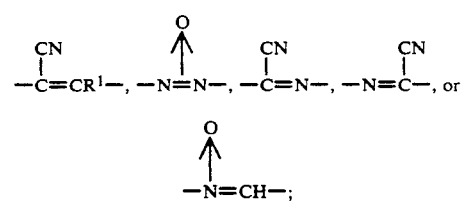

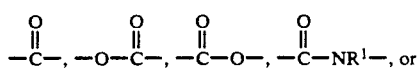

each A' is independently a divalent hydrocarbyl group having from 1 to about 10, preferably from 1 to about 4, carbon atoms; each A¹ is independently a $$-\overset{O}{\underset{\|}{C}}-, \ -O-\overset{O}{\underset{\|}{C}}-, \ -\overset{O}{\underset{\|}{C}}-O-, \ -\overset{O}{\underset{\|}{C}}-NR^1-, \text{ or}$$

$$-NR^1-\overset{O}{\underset{\|}{C}}- \text{ group;}$$

each R is independently hydrogen or a hydrocarbyl or hydrocarbyloxy group having from 1 to about 10, preferably 1 to about 4, carbon atoms, a halogen atom, preferably chlorine or bromine, a nitro group, a nitrile group, a phenyl group or a —CO—R¹ group; each R¹ is independently hydrogen or a hydrocarbyl group having 1 to about 3 carbon atoms; each R² is independently a hydrocarbyl group having from 1 to about 6 carbon atoms; z has a value of one or two; n has a value of zero or one; p has a value from zero to about 30, preferably from zero to about 5; and p¹ has a value from 1 to about 30, preferably from 1 to about 3. The aromatic rings or the A' hydrocarbyl group of Formula III can also contain one or more heteroatoms selected from N, O, S and the like.

The term hydrocarbyl as employed herein means any aliphatic, cycloaliphatic, aromatic, aryl substituted aliphatic or cycloaliphatic, or aliphatic or cycloaliphatic substituted aromatic groups. The aliphatic or cycloaliphatic groups can be saturated or unsaturated. When applied to the A' group of Formula III, the hydrocarbyl group can also contain one or more heteroatoms selected from N, O, S and the like. Likewise, the term hydrocarbyloxy means a hydrocarbyl group having an oxygen linkage between it and the carbon atom to which it is attached.

The epoxy resins containing a mesogenic moiety include, for example, those represented by the aforementioned Formulas I, II or III wherein at least 80 percent of the molecules are para substituted by both the bridging groups (—A—) and the substituent containing the epoxide or thiirane groups

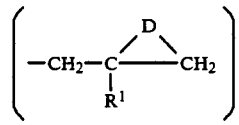

as well as the substituent containing a secondary hydroxyl or thiol alkylidene group(s)

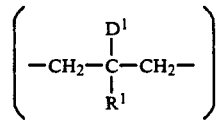

which are present when p has a value greater than zero.

The cyanate resins containing a mesogenic moiety include, for example, those represented by the aforementioned Formulas I, II or III wherein at least 80 percent of the molecules are para substituted by both the bridging groups (—A—) and the substituent containing the cyanate groups (—O—C≡N).

The vinyl ester resins containing a mesogenic moiety include, for example, those represented by the aforementioned Formulas I, II or III wherein at least 80 percent of the molecules are para substituted by both the bridging groups (—A—) and the substituent containing the vinyl ester groups

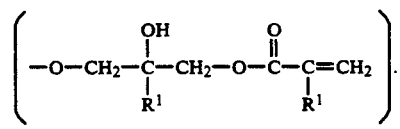

For Formula III, it is to be understood that para substitution is with respect to the direct bond between the aromatic rings. The bridging groups (—A—) form a rigid central linkage between the aromatic ring pairs. To optimize the aspect ratio of said mesogenic or rigid rodlike functionalities, it is preferred that the aromatic ring substituents (R in Formulas I, II and III) are hydrogen or methyl groups.

The term "mesogenic" as is used herein designates compounds containing one or more rigid rodlike structural units which have been found to favor the formation of liquid crystal phases in the case of low molar mass substances. Thus the mesogen or mesogenic moiety is that structure responsible for molecular ordering.

Representative epoxy resins containing a mesogenic moiety include, for example, the diglycidyl ethers and the dithiirane ethers of
4,4'-dihydroxybiphenyl, 4,4'-dihydroxystilbene, 4,4'-dihydroxy-diphenylacetylene, 4,4'-dihydroxydiphenylazomethine, 4,4'-dihydroxyazobenzene, 4,4'-dihydroxyazoxybenzene, 4,4'-bis((4-hydroxy)phenoxy)-diphenyl, 3,3', 5,5'-tetramethyl-4,4'-dihydroxydiphenyl, 3,3', 5,5'-tetrachloro-4,4'-dihydroxydiphenyl, 2,2',6,6'-tetramethyl-4,4'-dihydroxydiphenyl, bis (4-hydroxyphenyl)terephthalate, N,N'-bis(4-hydroxyphenyl)-terephthalamide, 4-hydroxyphenyl-4-hydroxybenzoate, 4,4'-dihydroxybenzanilide, N-methyl-4,4'-dihydroxybenzanilide, 4,4'-dihydroxyalphamethylstilbene, 4,4'-dihydroxychalcone, 4,4'-dihydroxyalpha-cyanostilbene, 2,2'-dimethyl-4,4'-dihydroxyazoxybenzene, 4,4'-dihydroxy-a,a,dimethylstilbene, 4,4''-dihydroxybiphenylbenzoate, 4,4''-dihydroxy-α,α'-diethylstilbene, bis(4'-hydroxyphenyl)1,4-benzenediimine, bis(4'-hydroxybiphenyl)terephthalate,
the diglycidyl ethers and the dithiirane ethers of the dihydric phenols represented by the following formulas:

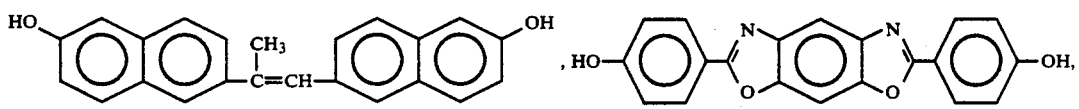

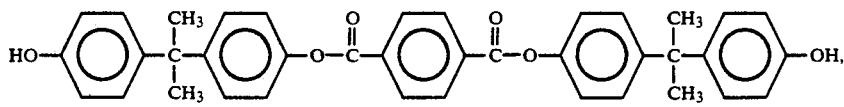

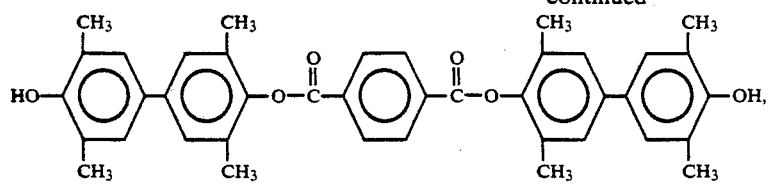
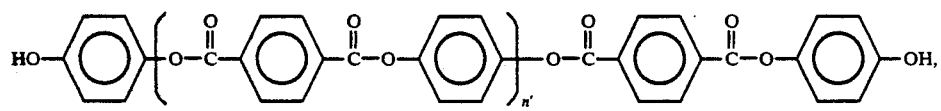
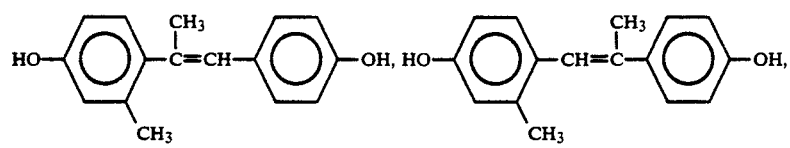
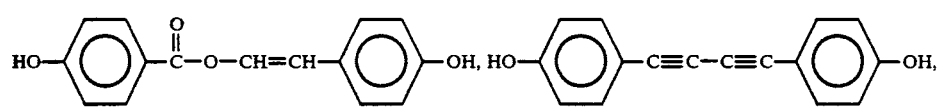
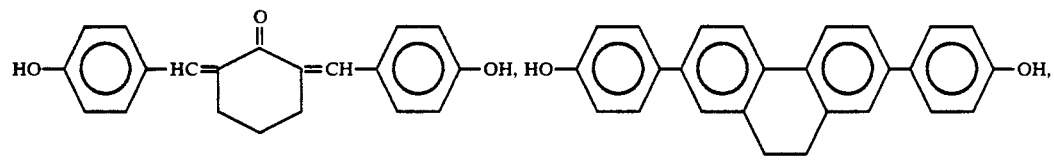
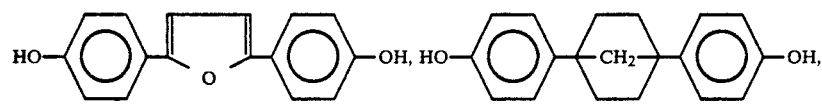
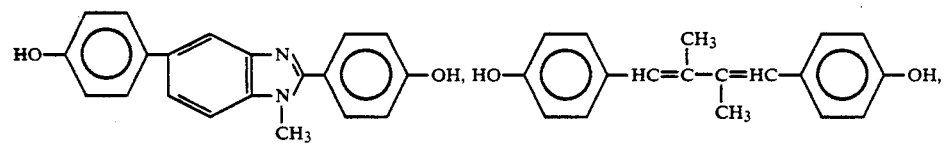
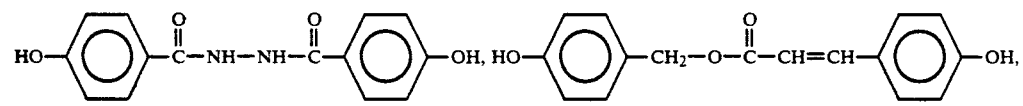
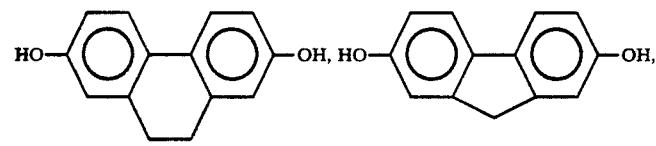
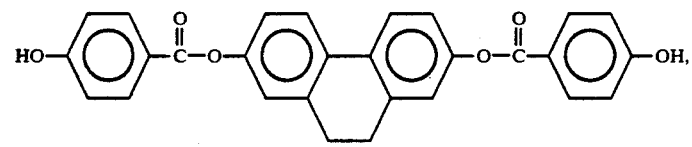
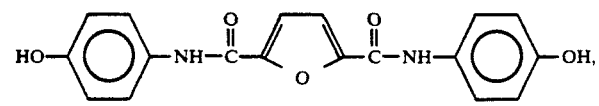

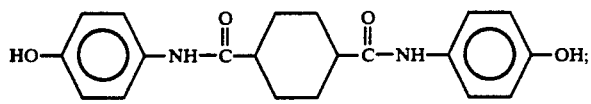

wherein n' has a value from 1 to about 10. Also suitable are the products resulting from advancing the aforementioned diepoxides or dithiiranes with aromatic dihydroxyl or carboxylic acid containing compounds including, for example, all of the previously listed diphenol precursors to the diepoxides or dithiiranes containing a mesogenic moiety; mixtures thereof and the like.

Additional representative epoxy resins containing a mesogenic moiety include, for example, the diglycidyl amines and the dithiirane glycidyl amines of N,N'-diethyl-4,4'-diaminostilbene, N,N'-dimethyl-4,4'-diaminostilbene, N,N'-dimethyl-4,4'-diaminobenzanilide; N'-methyl-4'-aminophenyl-N-methyl-4-aminobenzoate, the diglycidyl thioethers and dithiirane glycidyl thioethers of 4,4'-stilbenedithiol, 4,4'-alphamethylstilbenedithiol, 4,4'-benzanilidedithiol; the diglycidyl esters and the d-thiirane glycidyl esters of 4,4'-stilbenedicarboxylic acid, 4,4'-alphamethylstilbenedicarboxylic acid, 4,4'-benzanilidedicarboxylic acid; the diglycidyl ethers and the dithiirane glycidyl ethers of the bi3(2-hydroxyethylether)s of 4,4'-dihydroxystilbene, 4,4'-dihydroxy-alpha-methylstilbene; the diglycidyl thioether ethers and the dithiirane glycidyl thioether ethers of the bis(2-hydroxyethylthioether)s of 4,4'-stilbenedithiol, 4,4'-alpha-methylstilbenedithiol; the diglycidyl ester ethers and the dithiirane glycidyl ester ethers of the bis(2-hydroxyethylester)s of 4,4'-stilbenedicarboxylic acid, 4,4'-alphamethylstilbenedicarboxylic acid; the diglycidyl amine ethers and the dithiirane glycidyl amine ethers of the bis(2-hydroxyethylamine)s of N,N'-dimethyl-4,4'-diaminostilbene, N,N'-diethyl-4,4'-diaminostilbene, N'-methyl-4'-aminophenyl-N-methyl-4-aminobenzoate; mixtures thereof and the like. Also suitable are the products resulting from advancing the aforementioned epoxy resins with aromatic dihydroxyl or dicarboxylic acid containing compounds.

Representative cyanate resins containing a mesogenic moiety include, for example, the dicyanates of the aforementioned mesogen-containing diphenols used to prepare the mesogen-containing diglycidyl ethers.

Representative vinyl ester resins containing a mesogenic moiety include, for example, the acrylic acid and methaerylic acid esters of the aforementioned mesogen-containing diglycidyl ethers.

Preparation of Epoxy Resins

Epoxidation of di- and polyhydroxy aromatic compounds (or di- and polycarboxylic acids or bis(secondary amino)aromatic compounds) used to prepare the epoxy resins used in the present invention can be performed by the known methods described in *Handbook of Epoxy Resins* by Lee and Neville, McGraw-Hill, 1967; Jpn. Kokai Tokkyo Koho JP 62 86,484 (87 96,484); EP 88-008358/92 and *Journal of Applied Polymer Science*, Vol. 23, 1355–1372 (1972) all of which are incorporated herein by reference. This usually includes reacting the respective di- or polyhydroxy aromatic compound (or di- and polycarboxylic acids or bis(-secondary amino)aromatic compound) with an excess of an epihalohydrin such as, for example, epichlorohydrin or methyl epichlorohydrin, at a temperature of from about 0° C. to about 1000° C., preferably from about 20° C. to about 65° C. followed by dehydrohalogenation with a basic-acting material such as, for example, an alkali metal hydroxide, typically sodium hydroxide, at a temperature of from about 0° C. to about 100° C., preferably from about 200° C. to about 65° C. and finally recovering the resulting glycidyl ether product. For the production of polyepoxides from di- and polyhydroxy aromatic compounds possessing functional groups or linkages that are sensitive to hydrolysis under the reaction conditions employed in certain epoxidation chemistries, alternate techniques of preparation may be employed. As a typical example, Dhein, et al. in U.S. Pat. No. 4,762,901 teaches preparation of the diglycidyl ether of the bi3phenol represented by the following formula

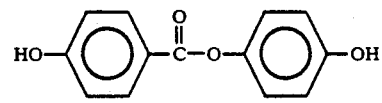

which is a compound containing an ester linkage known to be sensitive to hydrolysis, using an anhydrous epoxidation technique. This technique employs azeotropic removal of water/epichlorohydrin concurrent with the controlled addition of aqueous sodium hydroxide to a reaction mixture consisting of epichlorohydrin, a diphenol, a phase transfer catalyst such as, for example, benzyltrimethylammonium chloride, and optionally, solvent(s) may also be employed. It is advantageous to conduct such anhydrous epoxidation reactions under a vacuum to facilitate the azeotropic removal of water. The azeotropic removal of water is usually conducted at temperatures of from about 20° C. to about 100° C., preferably from about 30° C. to about 65° C. It is also operable and advantageous to utilize sodium hydroxide free of water as the alkali metal hydroxide reactant. In order to control reaction exotherm, the solid sodium hydroxide is typically added in aliquots as a powder to the epoxidation reaction mixture. A typical anhydrous epoxidation technique is described by Wang, et al. in U.S. Pat. No. 4,499,255 which is incorporated herein by reference in its entirety.

Another specific anhydrous epoxidation technique involves catalytic coupling of the di- or polyhydroxyl containing compound with an epihalohydrin, typically using as a catalyst one or more of the aforementioned ammonium halides. The resultant solution of halohydrin in excess epihalohydrin is then treated with finely pulverized potassium carbonate to effect dehydrohalogenation to the epoxy resin.

Epoxy resins can be converted to thiirane resins (polythiirane compounds) via reaction of the epoxide groups therein with suitable sulfur containing compounds such as, for example, inorganic thiocyanates, thioureas, N-alkylbenzothiazol-2-thiones such as N-methylbenzothiazol-2-thione/trifluoroacetic acid or a phosphine sulfide such as triphenylphosphine sulfide/-trifluoroacetic acid.

The reaction is usually conducted at temperatures of from about 5° C. to about 100° C., preferably from about 200° C. to about 60° C., for a time sufficient to complete the reaction, usually from about one hour to about forty eight hours, preferably from about four to about twenty four hours. The higher reaction temperatures typically require shorter times whereas the lower reaction temperatures typically require longer times to complete the reaction.

These reaction conditions are reported by Bell and Ku in the article "Epoxy/Episulfide Resins" pages 3 to 26 and by Vecera and Spacek in the article "Preparation and Reactivity of Thiiranes", pages 73 to 80 both published in *Crosslinked Epoxies*, Sedlacek and Kahwec (editors), by Walter de Gruyter, New York (1987); Chan and Finkenbine, *Journal of the American Chemical Society*, 94, 2880 (1972) and Calo, Lopez, Marchese and Pesce, *Journal of the Chemical Society, Chemical Communications*, 621 (1975), all of which are incorporated herein by reference.

Advanced Epoxy Resins

Advancement reaction of the epoxy resins containing a mesogenic moiety with one or more compounds having an average of more than one active hydrogen atom per molecule can be performed by the known methods described in the aforementioned *Handbook of Epoxy Resins*. This usually includes combining the compound(s) having an average of more than one group reactive with an epoxide or thiirane group per molecule and the epoxy resin(s) with the application of heat and mixing to effect the advancement reaction. A catalyst i3 frequently added to facilitate the advancement reaction.

The epoxy resin(s) and the compound(s) having an average of more than one group reactive with an epoxide or thiirane group per molecule are reacted in amounts which provide suitably from about 0.001:1 to about 0.95:1, more suitably from about 0.01:1 to about 0.7:1, most suitably from about 0.05:1 to about 0.50:1 active hydrogen atoms per epoxide or thiirane group.

By the term "compounds having an average of more than one active hydrogen atom per molecule" it is meant that the compound contains hydrogen atoms which are reactive with an epoxide or thiirane group.

Suitable compounds having an average of more than one active hydrogen atom per molecule which can be employed to prepare advanced resins useful in the present invention may contain one or more mesogenic moieties or may be free of said moieties. Suitable compounds having an average of more than one active hydrogen atom per molecule which can be employed to prepare the advanced resins include, for example, diphenols, thiodiphenols, dicarboxylic acids and compounds containing one primary amine or amide group or two secondary amine groups such as those represented by the Formulas IV, V, VI or VII;

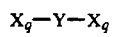

Formula IV

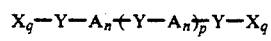

Formula V

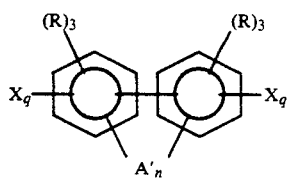

Formula VI $H_2N-R^3$  Formula VII wherein X is independently a —OH, —COOH, —SH or —NHR$^1$ group; q has a value of 1 with the proviso that when one q=1 and one q=0, one X may be —NH$_2$, ~H$_2$N—SO$_2$—, ~H$_2$N—CO— or H$_2$N—R$^3$—O— and the other X becomes R; R$^3$ is an aliphatic, cycloaliphatic, polycycloaliphatic or alkylsubstituted cycloaliphatic or polycycloaliphatic group having from 1 to about 12, preferably 1 to about 4, carbon atoms, q has a value of zero or one, each Y is independently

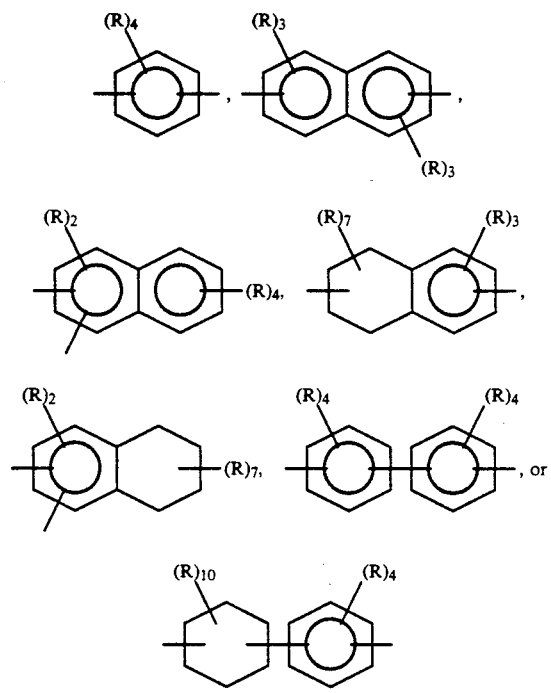

each A is independently a direct single bond, a divalent hydrocarbyl group having from 1 to about 20, preferably from 1 to about 14, carbon atoms, —O—, —CO—, —SO—, —SO$_2$—, —S—, —S—S—, —CR$^1$=CR$^1$—, —C≡C—, —N=N—, —CR$^1$=N—, —O—CO—, —NR$^1$—CO—, —CR$^1$=N—N=CR$^1$—, —CR$^1$=C- R$^1$—CO—, —N=CR$^1$—, —CO—O—, —CO—NR$^1$—, —CO—CR$^1$=CR$^1$—, —CO—O—N=CR$^1$, —CR$^1$=N—O—OC—, —CO—NR$^1$—OC—, —CR$^1$=C- R$^1$—O—OC—, —CO—O—CR$^1$=CR$^1$, —O—O- C—CR$^1$=CR$^1$—, —CR$^1$=CR$^1$—CO—O—, —CH- R$^1$—O—CO—CR$^1$=CR$^1$—, —CR$^1$=C- R$^1$—CO—O—CHR$^1$—, —CHR$^1$—CO—O—CR$^1$=C- R$^1$—, —CR$^1$=CR$^1$—O—CO—CHR$^1$, —CO—S—, —S—OC—, —CH$_2$—CH$_2$—CO—O—, —O—O- C—CH$_2$—CH$_2$—, —C≡C—C≡C—, —CR$^1$=C- R$^1$—CR$^1$=CR$^1$—,

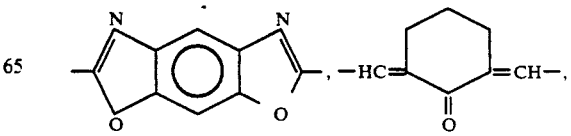

-continued

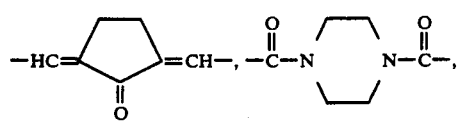

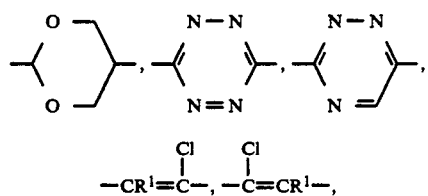

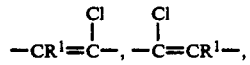

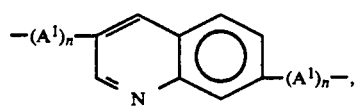

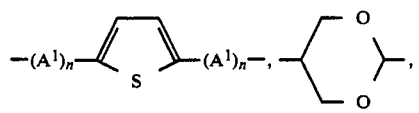

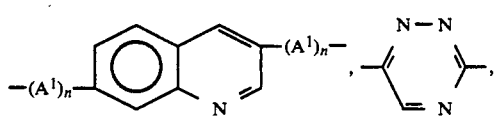

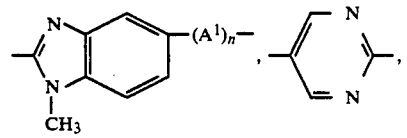

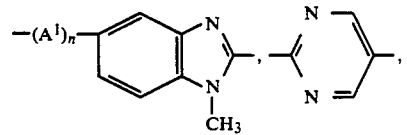

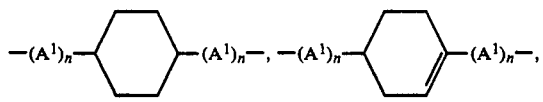

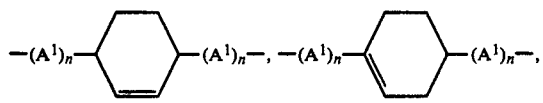

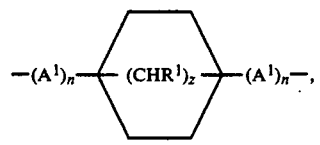

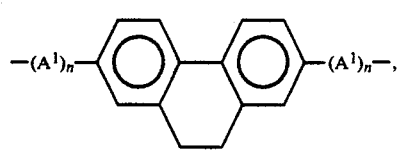

-continued

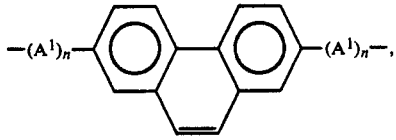

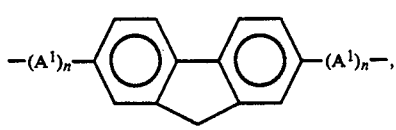

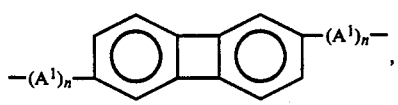

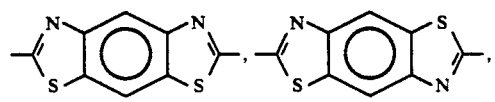

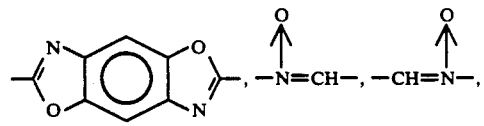

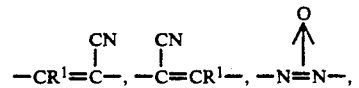

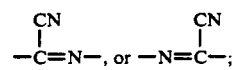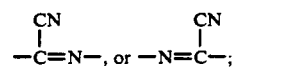

and A′, $A^1$, $R^1$, z and n are as hereinbefore defined. The aromatic rings can also contain one or more heteroatoms selected from N, O, S and the like.

Particularly suitable hydroxyl containing compounds include, for example, hydroquinone, bisphenol A, 4,4′-dihydroxydiphenylmethane, 4,4′-thiodiphenol, 4,4′-sulfonyldiphenol, 4,4′-dihydroxydiphenyl oxide, 4,4′-dihydroxybenzophenone, 1,1-bis(4-hydroxyphenyl)-1-phenylethane, 3,3′,5,5′-tetrachorobisphenol A, 3,3′-dimethoxybisphenol A, 4,4′-dihydroxybiphenyl, 4,4′-dihydroxy-α,α′-diethylstilbene, 4,4′-dihydroxy-α-methylstilbene, 4,4′-dihydroxybenzanilide, 4,4′-dihydroxy-2,2′-dimethylazoxybenzene. 4,4′-dihydroxy-α-cyanostilbene, bis(4-hydroxyphenyl)terephthalate, N,N′-bis(4-hydroxyphenyl)terephthalamide, bis(4′-hydroxybiphenyl)terephthalate, 4,4′-dihydroxyphenylbenzoate, bis(4′-hydroxyphenyl)-1,4-benzenediimine, 4,4″-dihydroxybiphenylbenzoate, 1,4-bis(4′-hydroxyphenyl-1′-carboxamide)benzene, 1,4-bis(4′-hydroxyphenyl-1′-carboxy)benzene, 4,4′-bis(4″-hydroxyphenyl-1″-carboxy)biphenyl, mixtures thereof and the like.

Particularly suitable thiol containing compounds include, for example, 4,4′-dithiodiphenylmethane, 4,4′-isopropylidenedithiophenol, 4,4′-dithio-α-methylstilbene, mixtures thereof and the like.

Particularly suitable carboxylic acid containing compounds include, for example, terephthalic acid, 4,4′-benzanilide dicarboxylic acid, 4,4′-phenylbenzoate dicarboxylic acid, 4,4′-stilbenedicarboxylic acid and mixtures thereof and the like.

Particularly suitable primary amine or amide containing compounds or compounds containing two secondary amine groups include, for example, aniline, 4'-sulfonamido-N-phenylbenzamide, 4'-sulfonamido-N'-phenyl-4-chlorobenzamide, 4-amino-1-phenylbenzoate, 4-amino-N-phenylbenzamide, N-phenyl-4-amino-phenyl-1-carboxamide, phenyl-4-aminobenzoate, biphenyl-4-aminobenzoate, 1-phenyl-4'-aminophenyl-terephthalate, N,N'-dimethyl-4,4'-diaminostilbene, or any mixture thereof and the like.

The advancement reaction can be conducted in the presence of a suitable advancement catalyst such as, for example, phosphines, quaternary ammonium compounds, phosphonium compounds, tertiary amines and the like. Particularly suitable catalysts include, for example, ethyltriphenylphosphonium chloride, ethyltriphenylphosphonium bromide, ethyltriphenylphosphonium iodide, ethyltriphenylphosphonium diacetate (ethyltriphenylphosphonium acetate-acetic acid complex), ethyltriphenylphosphonium phosphate, tetrabutylphosphonium chloride, tetrabutylphosphonium bromide, tetrabutylphosphonium iodide, tetrabutylphosphonium diacetate (tetrabutylphosphonium acetate-acetic acid complex), butyltriphenylphosphonium tetrabromobisphenate, butyltriphenylphosphonium bisphenate, butyltriphenylphosphonium bicarbonate, benzyltrimethylammonium chloride, tetramethylammonium hydroxide, triethylamine, tripropylamine, tributylamine, 2-methylimidazole, benzyldimethylamine, mixtures thereof and the like. Many of these catalysts are described in U.S. Pat. Nos. 3,306,872; 3,341,580; 3,379,684; 3,477,990; 3,547,881; 3,637,590; 3,843,605; 3,948,855; 3,956,237; 4,048,141; 4,093,650; 4,131,633; 4,132,706; 4,171,420; 4,177,216 and 4,366,295, all of which are incorporated herein by reference.

The amount of advancement catalyst depends upon the particular reactants and catalyst employed; however, it is usually employed in quantities of from about 0.03 to about 3, preferably from about 0.03 to about 1.5, most preferably from about 0.05 to about 1.5 percent by weight based upon the weight of the epoxide or thiirane containing compound.

The advancement reaction can be conducted at atmospheric, superatmospheric or subatmospheric pressures at temperatures of from about 20° C. to about 260° C., preferably from about 80° C. to about 240° C., more preferably from about 100° C. to about 200° C. The time required to complete the advancement reaction depends upon the temperature employed. Higher temperatures require shorter periods of time whereas lower temperatures require longer periods of time. Generally, however, times of from about 5 minutes to about 24 hours, preferably from about 30 minutes to about 8 hours, more preferably from about 30 minutes to about 3 hours are suitable.

If desired, the advancement reaction can be conducted in the presence of one or more solvents. Suitable such solvents include, for example, glycol ethers, aliphatic and aromatic hydrocarbons, aliphatic ethers, cyclic ethers, ketones, esters, amides, combinations thereof and the like. Particularly suitable solvents include, for example, toluene, benzene, xylene, methyl ethyl ketone, methyl isobutyl ketone, diethylene glycol methyl ether, dipropylene glycol methyl ether, dimethylformamide, dimethylsulfoxide, N-methylpyrrolidinone, tetrahydrofuran, propylene glycol methyl ether, combinations thereof and the like. The solvents can be employed in amounts of from about zero to about 80%, preferably from about 20% to about 60%, more preferably from about 30% to about 50% by weight based upon the weight of the reaction mixture.

The advancement of the epoxy resins containing one or more mesogenic moieties with compounds having an average of more than one active hydrogen atom per molecule is employed to chain extend and/or branch the resin. This chain extension and/or branching is required for some mesogen containing resin compositions in order to obtain liquid crystal character. The advancement of the mesogenic epoxy resins can also be used to modify the temperature range in which a particular resin is liquid crystalline and to control the degree of crosslinking during the final curing.

Preparation of Cyanate Resins

The polycyanates used in the present invention are prepared by reacting one or more polyphenols containing one or more mesogenic moieties with a stoichiometric quantity or a slight stoichiometric excess (up to about 20 percent excess) of a cyanogen halide per —OH group in the presence of a stoichiometric quantity or a slight stoichiometric excess (up to about 20 percent excess) of a base compound per —OH group and in the presence of a suitable solvent.

Reaction temperatures of from about −40° C. to about 60° C. are operable, with reaction temperatures of −15° C. to 10° C. being preferred. Reaction times can vary substantially, for example, as a function of the reactants being employed, the reaction temperature, solvent(s) used, the scale of the reaction, and the like, but are generally between 15 minutes and 4 hours, with reaction times of 30 minutes to 90 minutes being preferred.

Suitable cyanogen halides include cyanogen chloride and cyanogen bromide. Alternately, the method of Martin and Bauer described in *Organic Synthesis,* Volume 61, pages 35 to 68 (1983) published by John Wiley and Sons can be used to prepare the required cyanogen halide in situ from sodium cyanide and a halogen such as chlorine or bromine.

Suitable base compounds include both inorganic bases and tertiary amines such a3 sodium hydroxide, potassium hydroxide, trimethylamine, triethylamine, mixtures thereof, and the like. Triethylamine is most preferred as the base.

Suitable solvents for the cyanation reaction include water, aliphatic ketones, chlorinated hydrocarbons, aliphatic and cycloaliphatic ethers and diethers, aromatic hydrocarbons, mixtures thereof and the like. Acetone, methylethyl ketone, methylene chloride and chloroform are most preferred as the solvent.

Preparation of Vinyl Ester Resins

The vinyl ester resins used in the present invention are prepared by reacting one or more diglycidyl ethers, optionally containing one or more monoepoxides, containing one or more mesogenic moieties with one or more polymerizable monounsaturated monocarboxylic acids. A mole ratio of 0.9 to 1.1 monounsaturated monocarboxylic acid per epoxide group is preferred with a ratio of 0.95 to 1.0 being most preferred.

Suitable monounsaturated monocarboxylic acids for reaction with the diglycidyl ethers (optionally containing one or more monoepoxides) include, for example, acrylic acid, methaerylic acid, cyanoacrylic acid, crotonic acid, alpha-phenylacrylic acid, methoxyacrylic acid, alpha-4-phenylphenylacrylic acid, monomethylester of fumaric acid,

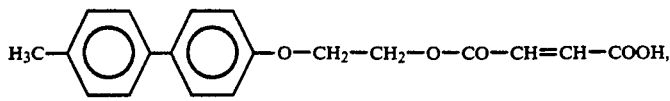

mixtures thereof and the like.

The reaction between the epoxide group and the carboxylic acid group is typically performed in the presence of one or more catalysts. Chromium trichloride and tris(dimethylaminoethyl)phenol are most preferred as the catalysts. A quantity of from about 0.01 to about 2 percent by weight has been found to be a suitable quantity of catalyst with concentrations of 0.1 to about 0.3 weight percent of the total reactants being most preferred.

A suitable process inhibitor is typically used in the reaction between the epoxide group and the carboxylic acid group to prevent gelation (homopolymerization of the vinyl ester(s) and/or copolymerization of the vinyl ester(s) with unreacted monounsaturated monocarboxylic acid). Hydroquinone activated with air is a most preferred inhibitor at concentrations of from about 100 ppm to about 500 ppm based on the weight of the total reactants used.

The reaction to produce the vinyl ester resins containing one or more mesogenic moieties is optionally conducted in one or more organic solvents inert to the other reactants. The term inert as applied to the organic solvent means that little, if any, reaction between the diglycidyl ether (optionally containing one or more monoepoxides), the monounsaturated monocarboxylic acid or the vinyl esters thereof occurs under the reaction conditions employed. Typical of the inert organic solvents are the aliphatic ketones, such as methylisobutyl ketone, the chlorinated aliphatics, such as perchloroethylene and the aromatic hydrocarbons, such as toluene.

The reaction to produce vinyl esters is usually conducted at a temperature of f rom about 50° C. to about 125° C., preferably from about 80° C. to about 120° C. for from about 90 minutes to about 720 minutes, preferably from about 120 minutes to about 420 minutes. Although reaction times and reaction temperatures can vary containing a mesogenic moiety are produced by reacting to a specific conversion, typically 1.5 to 0.25 percent carboxylic acid.

The resulting vinyl ester containing one or more mesogenic moieties can be combined with one or more polymerizable ethylenically unsaturated monomers. Suitable ethylenically unsaturated monomers which can be employed herein can be selected from the many known classes of polymerizable vinyl monomers. Suitable such monomers include, for example, the vinyl aromatic compounds which include such monomers as styrene, alphamethylstyrenes, vinyl toluenes, halogenated styrenes, t-butylstyrenes, divinylbenzenes and the like. Other suitable monomers include the methyl, ethyl, isopropyl, oetyl, etc. esters of acrylic or methacrylic acid; acidic monomers such as acrylic acid, methacrylic acid and crotonic acid; amide monomers such as acrylamide and N-alkylacrylamides; allyl monomers such as diallylphthalate, triallylisocyanurate, diallylmaleate and dimethallylfumarate; mixtures thereof and the like.

Preferred polymerizable monomers containing ethylenic unsaturation include, for example, styrene, p-vinyltoluene, o-, m-, p-halostyrenes, vinyl naphthalenes, vinyl acetate, the various alphasubstituted styrenes, as well as the various di-, triand tetrahalo styrenes and acrylic, methacrylic and crotonic acid esters including both the saturated alcohol esters and the hydroxyalkyl esters.

Curing Agents and/or Catalysts

The epoxy resins useful in the present invention can be cured with any suitable curing agent and/or curing catalyst for curing epoxy or thiirane resins such as, for example, primary and secondary polyamines, carboxylic acids and anhydrides thereof, aromatic hydroxyl containing compounds, imidazoles, guanidines, urea-aldehyde resins, melamine-aldehydes resins, alkoxylated urea-aldehyde resins, alkoxylated melamine-aldehyde resins, aliphatic amines, cycloaliphatic amines, aromatic amines, combinations thereof and the like. Particularly suitable curing agents include, for example, methylene dianiline, dicyandiamide, ethylene diamine, diethylenetriamine, triethylenetetramine, tetraethylenepentamine, urea-formaldehyde resins, melamine-formaldehyde resins, methylolated urea-formaldehyde resins, methylolated melamine-formaldehyde resins, phenol-formaldehyde novolac resins, cresol-formaldehyde novolac resins, 3ulfanilamide, substituted sulfanilamide3, diaminodiphenylsulfone, diethyltoluenediamine, t-butyltoluenediamine, bis-4-aminocyclohexylmethane, isophoronediamine, diaminocyclohexane, hexamethylenediamine, piperazine, aminoethylpiperazine, 2,5-dimethyl-2,5-hexanediamine, 1,12-dodecanediamine, tris-3-aminopropylamine, combinations thereof and the like.

The curing agents and/or curing catalysts are employed in amounts which will effectively cure the epoxy or thiirane resin; however, these amounts will depend upon the particular epoxy resin or thiirane resin and curing agent and/or curing catalyst employed. Generally, suitable amounts of curing agent include, for example, from about 0.50:1 to about 1.2:1, preferably from about 0.90:1 to about 1.1:1 equivalents of curing agent per equivalent of resin. Generally, suitable amounts or curing catalyst include, for example, from about 0.00001 to about 5, preferably from about 0.1 to about 1 weight percent of catalyst based on the weight of epoxy or thiirane resin.

The thiirane resins useful in the present invention can also be "self-cured", that is subjected to heat, until reaction of thiirane moieties occurs. It is felt that the self-curing results from initial opening of the thiirane ring to form a stable sulfide ion which subsequently anionically attacks another thiirane ring. It is beneficial to partially (B-stage) or totally homopolymerize (self-cure) the polythiiranes containing one or more mesogenic moieties to produce resin compositions possessing liquid crystal character.

The polycyanates useful in the present invention can be cured by heating from about 50° C. to about 400° C., preferably by heating from about 100° C. to about 250° C., optionally in the presence of a suitable catalyst. Suitable catalysts include, for example, acids, bases, salts, nitrogen and phosphorous compounds, such as for example, Lewis acids, such as AlCl$_3$, BF$_3$, FeCl$_3$, TiCl$_4$, ZnCl$_2$, SnCl$_4$:protonic acids such as HCl, H$_3$PO$_4$; aromatic hydroxy compounds such as phenol, p-nitrophenol, pyrocatechol, dihydroxynaphthalene; sodium hydroxide, sodium methylate, sodium phenolate, trimethylamine, triethylamine, tributylamine, diazabicyclo-(2.2.2)-octane, quinoline, isoquinoline, tetrahydroisoquinoline, tetraethylammonium chloride, pyridine-N-oxide, tributyl phosphine, zinc octoate, tin octoate, zinc naphthenate, cobalt naphthenate, cobalt acetylacetonate and the like. Also suitable as catalysts are the metal chelates such as, for example, the chelates of transition metals and bidentate or tridentate ligands, particularly chelates of iron, cobalt, zinc, copper, manganese, zirconium, titanium, vanadium, aluminum and mahnesium. These and other operable catalysts are disclosed in U.S. Pat. Nos. 3,694,410 and 4,094,852 which are incorporated herein by reference in their entirety. Cobalt naphthenate, cobalt octoate and cobalt acetylacetonate are most preferred as the catalysts. The quantity of catalyst used, if any, depends on the structure of the polycyanate being cured, the cure time, and the like. Generally, catalyst concentrations of from about 0.001 to about 2 percent weight are preferred.

B-staging or prepolymerization of the polycyanates used in the present invention can be accomplished by using lower temperatures and/or shorter cure times. Curing of the thus formed B-staged (prepolymerized) cyanate resin can then be accomplished at a later time or immediately following B-staging (prepolymerization) by increasing the temperature and/or curing time.

The vinyl ester compositions useful in the present invention can be cured by the application of heat and/or pressure, optionally in the presence of a free radical forming catalyst. Catalysts that can be used for the curing are preferably the peroxide catalysts, such as benzoyl peroxide, lauroyl peroxide, t-butylhydroperoxide, methylethylketone peroxide, t-butylperbenzoate, potassium persulfate, mixtures thereof and the like. The amount of the catalyst added will vary from 0.1 to about 2 percent by weight, preferably from 0.75 to 1.5 percent by weight. Temperatures employed can vary over a considerable range but usually are in the range of 20° C. to 250° C. Depending on the relative solubility and phase transition temperature(s) associated with the mesogenic moieties present in the vinyl ester compositions, curing at a elevated temperature can be especially desireable to enhance the molecular anisotropy of the cured product.

Additionally, more rapid curing of the vinyl ester compositions can be accomplished by the addition of accelerating agnets such as lead or cobalt naphthenate, N,N-dimethylaniline, mixtures thereof and the like, usually in concentrations ranging from about 0.01 to about 2 percent by weight, preferably 0.05 to 0.5 percent by weight.

Monoepoxide and Monothiirane Compounds

Monothiirane and/or monoepoxide compounds can be employed as reactive diluents for the epoxy or thiirane resins useful in the present invention. The monoepoxide and/or monothiirane compounds may contain one or more mesogenic moieties or may be free of said mesogenic moieties. Preparation of monothiirane compounds containing a mesogenic unit which can be employed as reactive diluents herein is taught by Scherowsky and Gay, *Liquid Crystals*, 5, 4, 1253 (1989) which is incorporated herein by reference.

The monoepoxide and/or monothiirane compound(s) are employed in amounts which provides the composition with the viscosity and reactivity profile desired for the particular purpose in which the composition is being employed. Usually the amount of monoepoxide and/or monothiirane compound(s) is from about 1 to about 99, preferably from about 5 to about 40, percent by weight based upon the combined weight of all compounds containing epoxide and/or thiirane groups.

Non-Mesogenic Thermosettable Resins

The mesogenic thermosettable resins used in the present invention can also be employed for the purpose of improving the properties provided by non-mesogenic thermosettable resins. Generally, suitable amounts of mesogenic thermosettable resins are from about 1 to about 99, more suitably from about 10 to about 80, most suitably from about 10 to about 50 weight percent based on the total weight of the combined resins.

Suitable epoxy resins which can be blended with the mesogenic resins include any compound containing an average of more than one vicinal, epoxide group per molecule. Suitable such epoxy resins include, for example, aromatic epoxides, aliphatic epoxides, and cycloaliphatic epoxides and the like. Particularly suitable epoxy resins include the diglycidyl ethers of: (a) compounds containing one or more aromatic rings and two or more aromatic hydroxyl groups per molecule; (b) compounds which are the result of reacting an alkylene oxide or monoglycidyl ether compound with the compounds of (a); (c) aliphatic diols which contain ether oxygen atoms or which are free of ether oxygen atoms; and (d) cycloaliphatic compounds containing more than one hydroxyl group per molecule.

Particularly suitable epoxy resins include, for example, (a) the diglycidyl ethers of resorcinol, bisphenol A, 4,4'-dihydroxydiphenylmethane, 4,4'-dihydroxybenzophenone, 3,3',5,5'-tetrabromobisphenol A, 4,4'-thiodiphenol, 4,4'-sulfonyldiphenol, 4,4'-dihydroxydiphenyl oxide, 1,1-bis(4-hydroxyphenyl)-1-phenylethane, 3,3',5,5'-tetrachlorobisphenol A, 3,3'-dimethoxybisphenol A, 4,4'-dihydroxy-alpha-methylstilbene, 4,4'-dihydroxybenzanilide, 4,4'-dihydroxyazoxybenzene, 4,4'-dihydroxybiphenyl; (b) the triglycidyl ether of tris(-hydroxyphenyl)methane; (c) the polyglycidyl ethers of a phenol or alkyl or halogen substituted phenolaldehyde acid catalyzed condensation product (novolac resins); the polyglycidyl ether of the condensation product of a dicyclopentadiene or an oligomer thereof a phenol or alkyl or halogen substituted phenol; (d) the advancement reaction products of the aforesaid diand polyglycidyl ethers with aromatic di- or polyhydroxyl- or carboxylic acid-containing compounds including, for example, bisphenol A (4,4'-isopropylidenediphenol), o-, m-, p-dihydroxybenzene, 2,4-dimethylresorcinol, 4,4'-dihydroxybiphenyl, 4,4'-dihydroxy-alpha-methylstilbene, 4,4'-dihydroxybenzanilide, 4-chlororesoreinol, tetramethylhydroquinone, 1,1-bis(4-hydroxyphenyl)ethane, 1,1-bis(4-hydroxyphenyl)-l-phenylethane, 4,4'-dihydroxydiphenyl ether, 3,3',5,5'-tetramethyldihydroxydiphenyl ether, 3,3',5,5'-dichlorodihydroxydiphenyl ether, 4,4'-bis-(p-hydroxyphenyl isopropyl)diphenyl ether, 4,4'-bis(p-hydroxyphenoxy)benzene, 4,4'-bis(p-hydroxyphenoxy)diphenyl ether, 4,4'-bis(4(4-hydroxyphenoxy)phenyl sulfone)diphenyl ether, 4,41-dihydroxydiphenyl sulfone, 4,4'-dihydroxydiphenyl sulfide, 4,4'- dihydroxydiphenyl disulfide, 2,2'-dihydroxydiphenyl sulfone, 4,4'-dihydroxydiphenyl methane, 1,1-bis(p-hydroxyphenyl)cyclohexane, 4,4'-dihydroxybenzophenone, phloroglucinol, pyrogallol, 2,2',5,5'-tetrahydroxydiphenyl sulfone, tris(hydroxyphenyl)methane, dicyclopentadiene diphenol, tricyclopentadiene diphenol; and (e) any combination of any of the aforementioned epoxy resins and the like.

Suitable cyanate resins which can be blended with the mesogenic resins include any compound containing an average of more than one cyanate group per molecule. Suitable such cyanate resins include; for example the aromatic di- and polycyanates and aromatic cyanate terminated oligomers and polymers. Particularly suitable cyanate resins are the aromatic dicyanates.

Particularly suitable cyanate resins include, for example, the dicyanates of the aforementioned mesogen-free diphenols used to prepare the mesogen-free epoxy resins.

Suitable vinyl ester resins which can be blended with the mesogenic resins include any compound containing an average of more than one vinyl ester group per molecule. Suitable such vinyl ester resins include, for example, vinyl esters of aromatic epoxides, aliphatic epoxides, and cycloaliphatic epoxides and the like. Particularly suitable vinyl esters include the vinyl esters of the diglycidyl ethers of: (a) compounds containing one or more aromatic rings and two or more aromatic hydroxyl groups per molecule; (b) compounds which are the result of reacting an alkylene oxide or monoglycidyl ether compound with the compounds of (a); (c) aliphatic diols which contain ether oxygen atoms or which are free of ether oxygen atoms; and (d) cycloaliphatic compounds containing more than one hydroxyl group per molecule.

Particularly suitable vinyl ester resins include, for example the vinyl ester resins of the aforementioned mesogen-free diglycidyl ethers, triglycidyl ether, polyglycidyl ethers and advancement reaction products of the aforesaid di- and polyglycidyl ethers.

Continuous Reinforcing Materials

The continuous reinforcing materials which can be employed herein include natural and synthetic fibers in the form of woven fabric, mats, monofilament, multifilament, unidirectional fibers, or any combination thereof and the like. Suitable reinforcing materials include glass, ceramics, nylon, rayon, cotton, aramid, carbon (graphite), silicon carbide, polybenzoxazoles, polyesters such as polyalkylene terephthalates, polyethylene, polypropylene, aluminum oxide, boron, combinations thereof, or hybrids thereof and the like.

The amount of continuous reinforcing fiber used in the composites of the present invention-can vary widely as a function of the type of thermosettable resin(s) used, the type of curing agent(s) and/or catalyst(s) used, the processing temperature(s) employed, the type of continuous reinforcing fiber used, the processing method(s) used, and other known variables. Generally, continuous reinforcing fibers can be employed in amounts suitably from about 0.5 to about 90, more suitably from about 1 to about 80, most suitably from about 2 to about 70 percent by weight based upon the weight of the total composite.

Composite Processing Methods

The methods for combining the continuous fiber reinforcement with the mesogenic thermoset resin are those known to the art for the preparation of continuous fiber reinforced composites. These methods are based on applying the thermosettable resin plus any curing agent and/or catalyst that is used as the matrix material to the continuous fiber reinforcement in the melted state, as a powder, or in a one or more solvents. In this processing, the combination of the continuous fiber reinforcement and the curable mesogenic thermoset resin system can be done to prepare ready to mold sheets (prepreg) which can be used immediately or stored and used at a later time to form the desired part. Alternatively, the shape of the final composite can be done during combination with the continuous fiber reinforcement, such as is done in resin transfer molding, filament winding and pultrusion. Detailed teaching of these processing methods can be found in *Fiber-Reinforced Composites:Materials, Manufacturing, and Design* by P. K. Mallick, Chapter 5, pages 319 to 379, published by Marcel Dekker, Inc., New York, N.Y. (1988) which is incorporated herein by reference.

After, and optionally before, the combination with the continuous fiber reinforcement, the curable mesogenic thermoset resin system is heated to a temperature where liquid crystallinity either exists or develops during curing. Upon obtaining a liquid crystal state for the matrix resin, flow induced shear is then produced between the interstices of the continuous fiber reinforcement by the application of pressure. Processing methods which allow for the application of pressure during consolidation of the composite include autoclaving and/or vacuum bag molding, compression molding, resin transfer molding and rolling. Detailed teaching of these processing methods can be found in the aforementioned *Fiber-Reinforced Composites: Materials, Manufacturing, and Design* reference. After producing flow induced shear, sufficient time is allowed for thermosetting to lock in the resultant orientation in the matrix resin. The temperature of the composite can then be raised, if required, to complete the cure of the matrix resin.

The temperature at which pressure is applied to induce orientation of the matrix resin depends principally upon the curable mesogenic thermoset resin system used. The temperatures which are typically employed preferably range from about 20° C. to about 2600° C., more preferably from about 60° C. to about 240° C., most preferably from about 80° C. to about 200° C.

For certain of the curable mesogenic thermoset resin systems, holding at a specific temperature is required before the application of flow induced shear. This is needed in order to develop liquid crystal character which occurs as a result of B-staging (prepolymerization) of the resin. The B-staging times which are typically encountered for development of liquid crystal character can range from about 1 minute to 24 hours or longer depending upon the particular curable mesogenic thermoset resin system used and the temperature employed.

The pressure required to produce flow induced shear of the matrix resin depends principally upon the viscosity of the curable mesogenic thermoset resin system while in the liquid crystal state. The pressures which are typically employed preferably range from about 0 to about 10,000 psig, more preferably from about 1 to about 1000 psig, most preferably from about 5 to about 100 psig.

Additional Orientation Methods

During processing and/or cure of the composite into a part, electric and/or magnetic fields can be applied for the purpose of further orienting or modifying the orientation of the liquid crystal moieties contained or developed therein and oriented by flow induced shear in the interstices of the continuous fiber reinforcement. As specific examples of these methods, Finkelmann, et al, *Macromol. Chem.*, Volume 180, pages 803 to 806 (March 1979) induced orientation in thermotropic methacrylate copolymers containing mesogenic side chain groups decoupled from the main chain via flexible spacers in an electric field. Orientation of mesogenic side chain groups decoupled from the polymer main chain via flexible spacers in a magnetic field has been demonstrated by Roth and Krueeke, *Macromol. Chem.*, Volume 187, pages 2655 to 2662 (November 1986). Magnetic field induced orientation of mesogenic main chain containing polymers has been demonstrated by Moore, et al, *ACS Polymeric Material Sciences and Engineering*, Volume 52, pages 84 to 86 (April-May 1985). Magnetic and electric field orientation of low molecular weight mesogenic compounds is discussed by W. R. Krigbaum in *Polymer Liquid Crystals*, pages 275 to 309 (1982) published by Academic Press, Inc. All of the above are incorporated herein by reference in their entirety.

Other Components

The mesogenic thermoset resin plus any curing agent and/or curing catalyst used in the present invention can be blended with other materials such as solvents or diluents, fillers, pigments, dyes, flow modifiers, thickeners, reinforcing agents, mold release agents, wetting agents, stabilizers, fire retardant agents, surfactants, combinations thereof and the like.

These additives are added in functionally equivalent amounts, e.g., the pigments and/or dyes are added in quantities which will provide the composition with the desired color; however, they are suitably employed in amounts of from about zero to about 20, more suitably from about 0.5 to about 5, most suitably from about 0.5 to about 3 percent by weight based upon the weight of the total blended composition.

Solvents or diluents which can be employed herein include, for example, hydrocarbons, ketones, glycol ethers, aliphatic ethers, cyclic ethers, esters, amides, combinations thereof and the like. Particularly suitable solvents or diluents include, for example, toluene, benzene, xylene, methyl ethyl ketone, methyl isobutyl ketone, diethylene glycol methyl ether, dipropylene glycol methyl ether, dimethylformamide, N-methylpyrrolidinone, tetrahydrofuran, propylene glycol methyl ether, combinations thereof and the like.

The modifiers such as thickeners, flow modifiers and the like can be suitably employed in amounts of from zero to about 10, more suitably from about 0.5 to about 6, most suitably from about 0.5 to about 4 percent by weight based upon the weight of the total composition.

Suitable fillers which can be employed herein include, for example, inorganic oxides, ceramic microspheres, plastic microspheres, glass microspheres, inorganic whiskers, $CaCO_3$, combinations thereof and the like.

The fillers can be employed in amounts suitably from about zero to about 50, more suitably from about 1 to about 25, most suitably from about 2 to about 10 percent by weight based upon the weight of the mesogenic thermoset resin plus any curing agent and/or curing catalyst used.

The following examples are illustrative of the present invention, but are not to be construed as to limiting its scope in any manner.

EXAMPLE 1

A. Synthesis of 4,4'-Dihydroxy-alphamethylstilbene

Phenol (752.8 grams, 8.0 moles), chloroacetone (384.77 grams, 4.0 moles as chloroacetone) and methylene chloride (600 grams) are added to a reactor and cooled to −10° C. with stirring under a nitrogen atmosphere. The chloroacetone used is a commercial grade containing 96.25% chloroacetone, 0.05% acetone, 3.05% 1,1-dichloroacetone and 0.60% mesityl oxide. Concentrated sulfuric acid (392.32 grams, 4.0 moles) is added dropwise to the stirred solution over a forty minute period and so as to maintain the reaction temperature between −11° C. and −9° C. After 150 minutes of post reaction between a −11° C. to −9° C. temperature range, the viscous, orange colored oil product is mixed with iced deionized water (1000 milliliters). The oil product is separated then washed with a second portion (1000 milliliters) and then a third portion (1000 milliliters) of deionized water. After separation, the recovered oil product is added to a pair of 2 liter beakers along with ethanol (250 milliliters) and stirred to provide solutions. Deionized water (250 milliliters) is added to the stirred solutions and heating commences. As the temperature of the mixture increases, the stirred mixture begins to clear. Each time clearing is observed, sufficient deionized water is added to induce cloudiness, followed by continuation of the mixing and heating. Once the temperature reaches 90° C., a massive precipitation of white crystalline plates occurs and is followed by immediate coalesence of the precipitated product to an oil. The oil layer is recovered by decantation of the water layer and ethanol (250 milliliters) is added. Deionized water is again added to the stirred solutions as heating commences, in an amount sufficient to induce cloudiness each time clearing is observed. Once the temperature reaches 70° C., a massive precipitation of white crystalline plates again occurs. At this time, stirring is stopped, sufficient deionized water is added to fill both of the beakers and the crystalline slurries are chilled to 4° C. and held therein for 16 hours. The crystalline product is recovered by filtration of the chilled crystalline slurries, added to a beaker along with deionized water (1000 milliliters), then stirred with heating to 100° C. After maintaining the stirred slurry at 100° C. for thirty minutes, the crystalline product is recovered by filtration then again combined with deionized water (1000 milliliters) and stirred with heating to 100° C. The crystalline product is recovered by filtration then dried in a vacuum oven at 1000° C. and 5 mm Hg to a constant weight of 478.8 grams. Proton magnetic resonance spectroscopy and infrared spectrophotometric analysis confirm the product structure.

B. Epoxidation of 4,4'-dihydroxy-alpha-methylstilbene 4,4'-Dihydroxy-alpha-methylstilbene (452.58 grams, 4.0 hydroxyl equivalents) prepared using the method delineated in A above, epichlorohydrin (1850.6 grams, 20.0 moles), deionized water (160.9 grams, 8.0 percent by weight of the epichlorohydrin used) and isopropanol (996.5 grams, 35 percent by weight of the epichlorohydrin used) are added to a reactor and heated to 50° C. with stirring under a nitrogen atmosphere. Once the 50° C. reaction temperature is achieved, sodium hydroxide (144.0 grams, 3.60 moles) dissolved in deionized water (576 grams) is added dropwise to the reactor over a 45 minute period and so as to induce an exothermic increase in temperature to 59° C., with subsequent maintenance of the temperature at 55° C. Ten minutes after completion of the aqueous sodium hydroxide addition, the stirring is stopped and the aqueous layer which separates from the reaction mixture is pipetted off and discarded. Stirring resumes and after a total of twenty minutes following completion of the initial aqueous sodium hydroxide addition, a second solution of sodium hydroxide (64.0 grams, 1.60 moles) dissolved in deionized water (256.0 grams) is added to the reactor over a twenty minute period with maintenance of the 55° C. reaction temperature. Fifteen minutes after completion of the aqueous sodium hydroxide addition, the recovered reaction mixture is added to a separatory funnel and washed with 1500 milliliters of deionized water. The separated organic layer is washed a second time (1500 milliliters deionized water), recovered and then rotary evaporated under vacuum to final conditions of 150° C. and 1 mm Hg for 120 minutes. The product is recovered (651.0 grams) as an off-white, crystalline solid having an epoxide equivalent weight (EEW) of 180.51.

C. Characterization of the Diglycidyl Ether of 4,4'-Dihydroxy-alpha-methylstilbene for Liquid Crystallinity Analysis of the diglycidyl ether from B above via crosspolarized light microscopy is completed using a microscope equipped with a programmable hot stage using a heating rate of 10° C. per minute. The results are reported in Table I.

TABLE I

| Cycle Designation | Observed Transition Temperatures (°C.) | Comments |
|---|---|---|
| First Heating | 30 | White, opaque, birefringent solid. |
| | 112 | First fluidity noted. |
| | 131 | Isotropization is complete. |
| First Cooling | 140 | Isotropic fluid. |
| | 94 | Nematic liquid crystal texture forms. |
| | 57 | First crystallization noted. |
| | 54 | Rapid crystal growth noted. |

The diglycidyl ether is a monotropic liquid crystal with a nematic texture observed in the microscopic analysis.

D. Preparation of Unidirectional Graphite Prepreg Tape Based on the Diglycidyl Ether of 4,4'-Dihydroxyalpha-methylstilbene and Sulfanilamide A portion (500.0 grams) of the diglycidyl ether of 4,4'-dihydroxy-alpha-methylstilbene from B above is transferred to a metal container and then placed in an oven which is preheated to 160° C. After melt of the resin is complete, the metal container is removed from the oven and placed in a heating mantle where heating at 150° C. is maintained. At a resin temperature of 150° C., sulfanilamide (119.2 grams) is added and dissolved in the resin with continuous stirring and maintenance of the 150° C. temperature. Once a homogeneous blend of resin and sulfanilamide is obtained, it is cooled to 90° C. by removing the metal container from the heating mantle then partially submerging it into an ambient temperature (23° C.) water bath. The resin blend, which is a translucent liquid at this stage of cure, is next transferred to a machine designed for preparing unidirectional graphite prepreg. The operating conditions for the prepreg machine are a nip temperature of 92° C. and a platen temperature of 139° C. The unidirectional graphite fiber used to prepare the tape is T-650/42 12K (unsized) manufactured by Amoco Performance Products, Inc. The unidirectional graphite tape obtained (1.05 feet × 42 feet) contained an average of 30.6 weight percent of the diglycidyl ether of 4,4'-dihydroxy-alpha-methylstilbene/sulfanilamide resin. This prepreg is collected between release paper on a cardboard roll and then stored at 0° F. before use in the preparation of composite panels.

E. Microscopic Observations for the Diglycidyl Ether of 4,4'-Dihydroxy-alpha-methylstilbene and Sulfanilamide During Cure to Determine the Suscep to Shear Induced Orientation A portion (4.7970 grams) of the diglycidyl ether of 4,4-dihydroxy-alpha-methylstilbene from B above is placed in an oven preheated to 150° C. After melt of the resin is complete sulfanilamide (1.1441 grams) is added to the resin and the mixture is stirred periodically. After eighteen minutes, all of the sulfanilamide is dissolved, then the homogeneous resin blend is removed from the oven and cooled to room temperature (23° C.). A sample of the resin and curing agent blend is placed between two glass slides and then inserted into a hot stage preheated to 129.4° C. The blend on the hot stage is viewed with an optical microscope at 70X magnification using a crosspolarized light source. After placing the blend on the hot stage, a non-birefringent, translucent liquid is observed. On holding at 129.4° C., a birefringent phase is produced after 23 minutes. With continued heating at 129.4° C., the birefringent phase increased and liquid crystal textures are observed. After forty five minutes at 129.4° C., shear is applied to the resin by moving the top glass slide in one direction while holding the bottom glass slide stationary. After this application of shear, unidirectional orientation of the liquid crystal domains is observed.

F. Fabrication of Oriented Composite from Unidirectional Graphite Tape

A composite is prepared by hand layup of eight plies of unidirectional graphite prepreg tape from D above into a 12 inch by 12 inch square. The square layup is then bagged in a vacuum system for processing in an autoclave. The configuration for the vacuum bag layup thus prepared consists of the layup sandwiched between fluoro release film and maintained therein with a tacky tape dam, followed by sandwiching between layers of textured release ply. On top of the layer of textured release ply designated to be the top of the assembly is laid a caul plate, followed by a breather followed by the outer nylon bagging. Under the layer of textured release ply designated to be the bottom of the assembly is the outer nylon bagging. A bleeder is positioned at the Junction of the bottom fluoro release film and textured release ply layers. The vacuum bagged composite i3 processed and cured in an autoclave using the following parameters in the order delineated:

| Action | Pressure, psig (kg/cm²) | Temp., °F. (°C.) | Time, min |
|---|---|---|---|
| Ramp temperature from ambient (72° F.) | 0 (0) | 265 (129.4) | 25 |
| Hold Temperature | 0 (0) | 265 (129.4) | 45 |
| Ramp pressure from ambient | 80 (5.625) | 265 (129.4) | 15 |
| Hold | 80 (5.625) | 265 (129.4) | 180 |
| Ramp temperature from 248° F. | 80 (5.625) | 460 (237.8) | 120 |
| Hold | 80 (5.625) | 460 (237.8) | 60 |
| Cool down | 80 (5.625) | 72 (22.2) | 40 |
| Pressure down | 0 (0) | 72 (22.2) | 5 |

The 45 minutes of hold time at 265° F. (129.4° C.) is a minimum time for this particular curable resin to achieve adequate liquid crystallinity for subsequent orientation by shear stresses caused by forcing flow into the interstices between the graphite fibers.

G. Mechanical Property Testing

Flexural properties of test pieces prepared from the composite prepared in F above are determined using an Instron machine and standard test methods (ASTM D 790). The test pieces prepared from the composite are obtained from the longitudinal (fiber) direction and from the transverse (perpendicular to fiber) direction. The results are given in Table II.

COMPARATIVE EXPERIMENT A

Fabrication of Composite from Unidirectional Graphite Prepreg Tape Possessing Minimum Orientation Composite is prepared by hand layup using the method and materials of Example 1-F. The vacuum bagged composite is processed and cured in an autoclave using the following parameters in the order delineated:

| Action | Pressure, psig (kg/cm²) | Temp., °F. (°C.) | Time, min |
|---|---|---|---|
| Ramp temperature from ambient (72° F.) | 0 (0) | 85 (29.4) | 0 |
| Hold Temperature and ramp pressure from ambient (0 psi) | 10 (0.703) | 85 (29.4) | 5 |
| Hold pressure and ramp temperature | 10 (0.703) | 265 (129.4) | 25 |
| Hold temperature and ramp pressure | 85 (5.976) | 265 (129.4) | 180 |
| Hold pressure and ramp temperature | 85 (5.976) | 460 (237.8) | 120 |
| Hold | 85 (5.976) | 460 (237.8) | 60 |
| Cool down | 85 (5.976) | 85 (29.4) | 40 |
| Pressure down | 0 (0) | 85 (29.4) | 5 |

Flexural properties of test pieces prepared from the composite are determined using the method of Example 1-F. The test pieces prepared from the composite are obtained from the longitudinal (fiber) direction and from the transverse (perpendicular to fiber) direction. The results are given in Table II.

TABLE II

| | LONGITUDINAL | | TRANSVERSE | |
|---|---|---|---|---|
| | Flexural Modulus, psi (kg/cm²) | Flexural Strength, psi (kg/cm²) | Flexural Modulus, psi (kg/cm²) | Flexural Strength, psi (kg/cm²) |
| Ex. 1-G | 2,300,000 (161,706) | 235,000 (16,522) | 1,420,000 (99,836) | 15,800 (1,111) |
| Comp. Expt. A | 1,800,000 (126,553) | 220,000 (15,468) | 980,000 (68,901) | 12,500 (879) |

What is claimed is:

1. A method for forming a continuous fiber reinforced oriented mesogen-containing resin matrix composite which method comprises
   (A) saturating a continuous fiber substrate material with a curable composition comprising
      (1) at least one mesogen-containing resin which contains an average of more than one vicinal epoxide group, thiirane group, cyanate group or vinyl ester group per molecule; and, optionally
      (2) a curing amount of at least one curing agent and/or curing catalyst therefor;
   (B) arranging one or more saturated continuous fiber substrate materials formed in step (A) into a desired configuration;
   (C) heating the arranged saturated continuous fiber substrate material(s) from step (B) to a temperature which causes the mesogen-containing resin to convert to a liquid crystalline state;
   (D) subjecting the heated arranged saturated continuous fiber substrate material(s) from step (C) to a pressure sufficient to cause flow induced shear in interstices of said continuous fiber substrate materials;
   (E) subjecting the continuous fiber substrate material(s) of step (D) to curing conditions either simultaneously with the application of pressure in step (D) and/or subsequent to said application of pressure; and
   (F) permitting the cured continuous fiber substrate material(s) of step (E) to cool to room temperature; thereby forming a cured continuous fiber reinforced composite containing an oriented mesogen-containing resin matrix.

2. A method of claim 1 wherein component (A1) is a mesogen-containing resin which contains an average of more than one vicinal epoxide or thiirane group per molecule; step (C) is conducted at a temperature of from about 20° C. to about 260° C.; and step (D) is conducted at a pressure of from about 0 to about 10,000 psig.

3. A method of claim 2 wherein component (A1) is a mesogen-containing resin which contains an average of more than one vicinal epoxide or thiirane group per molecule represented by the Formulas I, II or III;

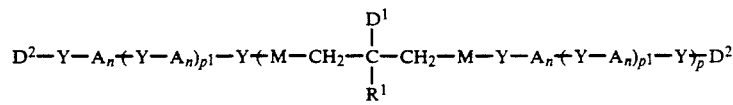

Formula I

Formula II

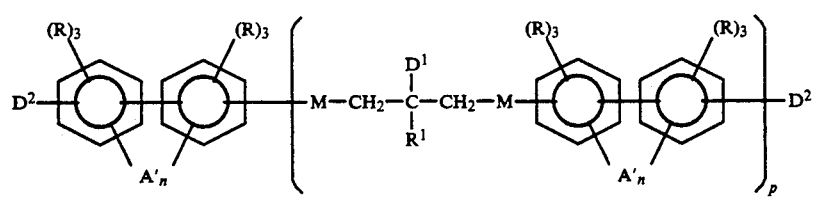

Formula III

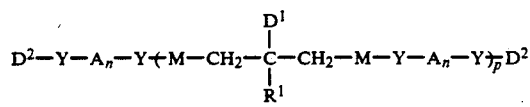

wherein each Y is independently

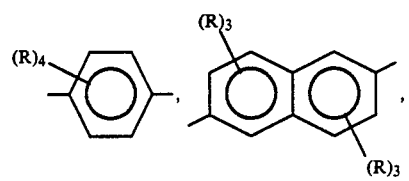,

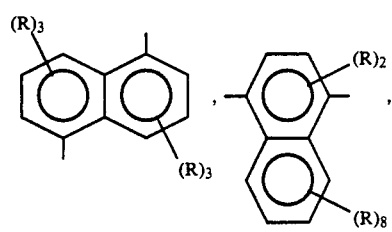,

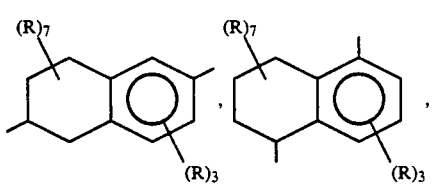,

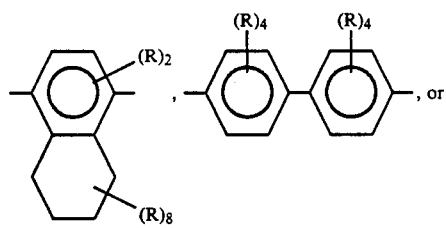, or

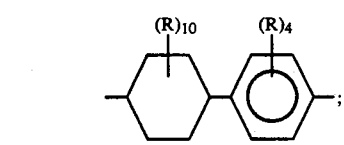;

D is —O— or —S—; D¹ is —OH or —SH; D² is

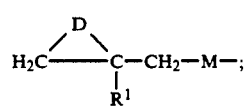;

each M is independently (a) —O—, —S—, —NR²—, or —CO—O— where the single bonded oxygen atom attached to the carbon atom of —CO—O— is attached to the

 group, or (b)

—CO—O$+$(CHR$^a$—CHR$^a$—O$)_{\overline{m}}$,

—O$+$CHR$^a$—CHR$^a$—O$)_{\overline{m}}$, or —S$+$(CHR$^a$—CHR$^a$—O$)_{\overline{m}}$ where a single bonded oxygen atom is attached to the

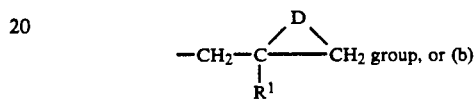 group;

each R$^a$ is independently hydrogen or an alkyl or haloalkyl group containing from 1 to about 2 carbon atoms with the proviso that only one R$^a$ group can be a haloalkyl group; m has a value from 1 to about 100; each A is independently a direct single bond, —CR¹=CR¹—, —C≡C—, —N=N—, —CR¹=N—, —O—CO—, —NR¹—CO—, —CR¹=N—N=CR¹—, —CR¹=CR¹—CO—, —N=CR¹—, —CO—O—, —CO—NR¹—, —CO—CR¹=CR¹—, —CO—O—N=CR¹—, —CR¹=N—O—OC—, —CO—NR¹—NR¹—OC—, —CR¹=CR¹—O—OC—, —CO—O—CR¹=CR¹—, —O—OC—CR¹=CR¹—, —CR¹=CR¹—CO—O—, —CHR¹—O—CO—CR¹=CR¹—, —CR¹=CR¹—CO—O—CHR¹—, —CHR¹—CO—O—CR¹=CR¹—, —CR¹=CR¹—O-CO-CHR¹—, —CO—S—, —S—OC—, —CH₂—CH₂—CO—O—, —O-O-C—CH₂—CH₂—, —C≡C—C≡C—, —CR¹=CR¹—CR¹=CR¹—,

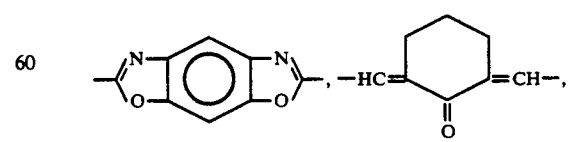

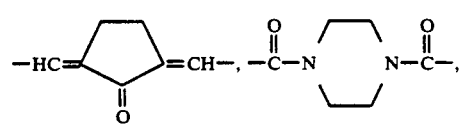

-continued

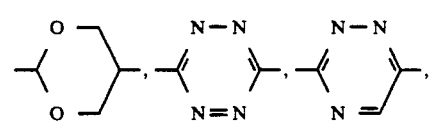

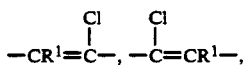

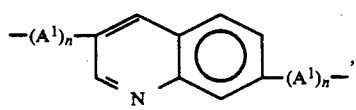

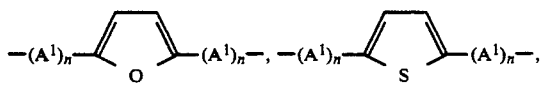

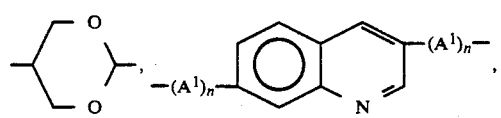

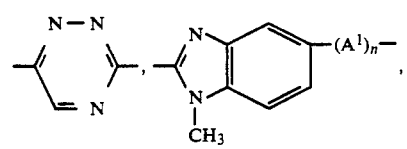

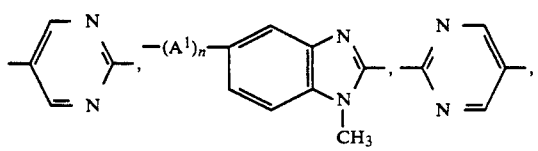

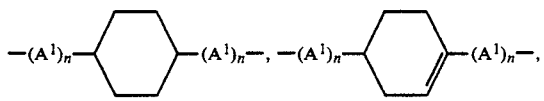

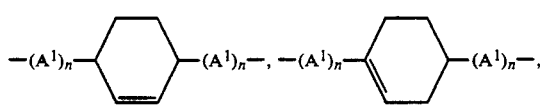

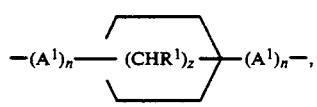

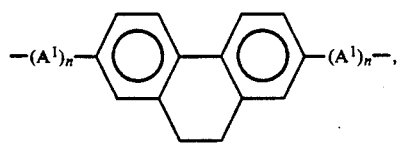

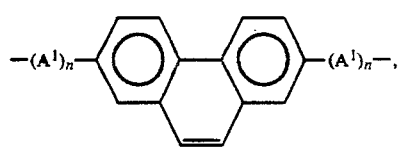

-continued

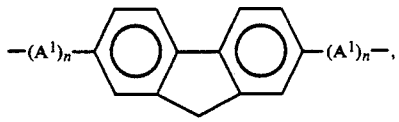

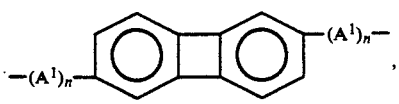

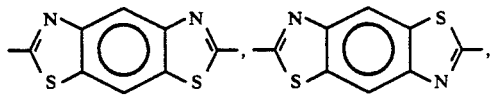

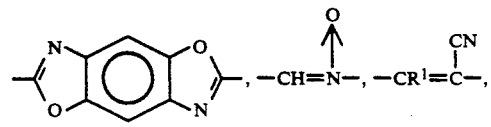

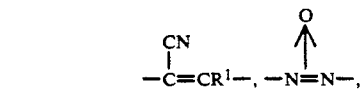

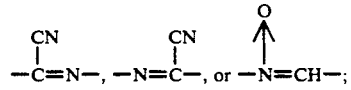

each A' is independently a divalent hydrocarbyl group having from 1 to about 10 carbon atoms and can contain an N, O or S heteroatoms; each $A^1$ is independently a

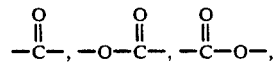

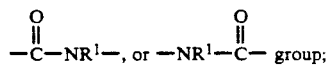

each R is independently hydrogen or a hydrocarbyl or hydrocarbyloxy group having from 1 to about 10 carbon atoms, a halogen atom, preferably chlorine or bromine, a nitro group, a nitrile group, a phenyl group or a —CO—$R^1$ group; each $R^1$ is independently hydrogen or a hydrocarbyl group having 1 to about 3 carbon atoms; each $R^2$ is independently a hydrocarbyl group having from 1 to about 6 carbon atoms; z has a value of one or two; n has a value of zero or one; p has a value from zero to about 30; and $p^1$ has a value from 1 to about 30; and the aromatic rings or the A' group in Formula III can also contain one or more heteroatoms selected from N, O, or S, with the proviso that at least 80 percent of the molecules are para substituted by both the bridging groups (-A-) and the substituent containing the epoxide or thiirane groups

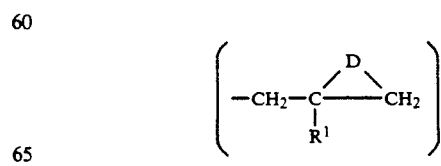

as well as the substituent containing a secondary hydroxyl or thiol alkylidene group(s)

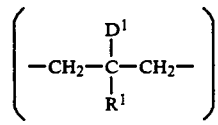

which are present when p has a value greater than zero.

4. A method of claim 3 wherein
(a) component (A1) is the diglycidyl ether of 4,4'-dihydroxy-alpha-methylstilbene or a blend of the diglycidyl ether of dihydroxy-alpha-methylstilbene and the diglycidyl ether of 4,4'-isopropylidenediphenol; and
(b) component (A2) is sulfanilamide, a substituted ulfanilamide, or any combination thereof.

* * * * *